(12) United States Patent
Isshiki et al.

(10) Patent No.: US 11,662,307 B2
(45) Date of Patent: May 30, 2023

(54) OPTICAL CONCENTRATION MEASURING DEVICE, MODULE FOR OPTICAL CONCENTRATION MEASURING DEVICE AND OPTICAL CONCENTRATION MEASURING METHOD

(71) Applicant: Asahi Kasei Microdevices Corporation, Tokyo (JP)

(72) Inventors: Shota Isshiki, Tokyo (JP); Edson Gomes Camargo, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 0 days.

(21) Appl. No.: 17/656,923

(22) Filed: Mar. 29, 2022

(65) Prior Publication Data
US 2022/0307976 A1    Sep. 29, 2022

(30) Foreign Application Priority Data

Mar. 29, 2021  (JP) .............................. JP2021-056034
Mar. 10, 2022  (JP) .............................. JP2022-037590

(51) Int. Cl.
*G01N 21/3504*    (2014.01)
*G01N 33/00*    (2006.01)

(52) U.S. Cl.
CPC ..... *G01N 21/3504* (2013.01); *G01N 33/0027* (2013.01); *G01N 2201/08* (2013.01)

(58) Field of Classification Search
CPC ........... G01N 21/3504; G01N 33/0027; G01N 2021/3545
See application file for complete search history.

(56) References Cited

U.S. PATENT DOCUMENTS

| | | | |
|---|---|---|---|
| 8,178,832 B1 | 5/2012 | Wong | |
| 10,788,415 B2* | 9/2020 | Shibuya | ............... G01N 21/031 |
| 2003/0034454 A1 | 2/2003 | Nomura et al. | |
| 2017/0102324 A1 | 4/2017 | Yasuda | |
| 2022/0307975 A1* | 9/2022 | Camargo | ............. G01N 21/314 |

FOREIGN PATENT DOCUMENTS

| | | |
|---|---|---|
| JP | 2003057178 A | 2/2003 |
| JP | 2004101416 A | 4/2004 |
| JP | 2004138499 A | 5/2004 |
| JP | 2014142319 A | 8/2014 |
| WO | 2016002468 A1 | 1/2016 |

* cited by examiner

*Primary Examiner* — David P Porta
*Assistant Examiner* — Meenakshi S Sahu
(74) *Attorney, Agent, or Firm* — Kenja IP Law PC

(57) ABSTRACT

The optical concentration measuring device 1 includes: a first optical filter 41; a second optical filter 42; and an operation part 60, wherein a difference between a peak wavelength of the first effective sensitivity spectrum based on the first transmission band in the first light receiving part 51 and a peak wavelength of the second effective sensitivity spectrum based on the second transmission band in the second light receiving part 52 is ±0.2 times or more and ±0.8 times or less the full width at half maximum of the first effective sensitivity spectrum, wherein the operation part removes an attenuation amount of the first intensity by the interference gas and an attenuation amount of the second intensity by the interference gas.

9 Claims, 8 Drawing Sheets

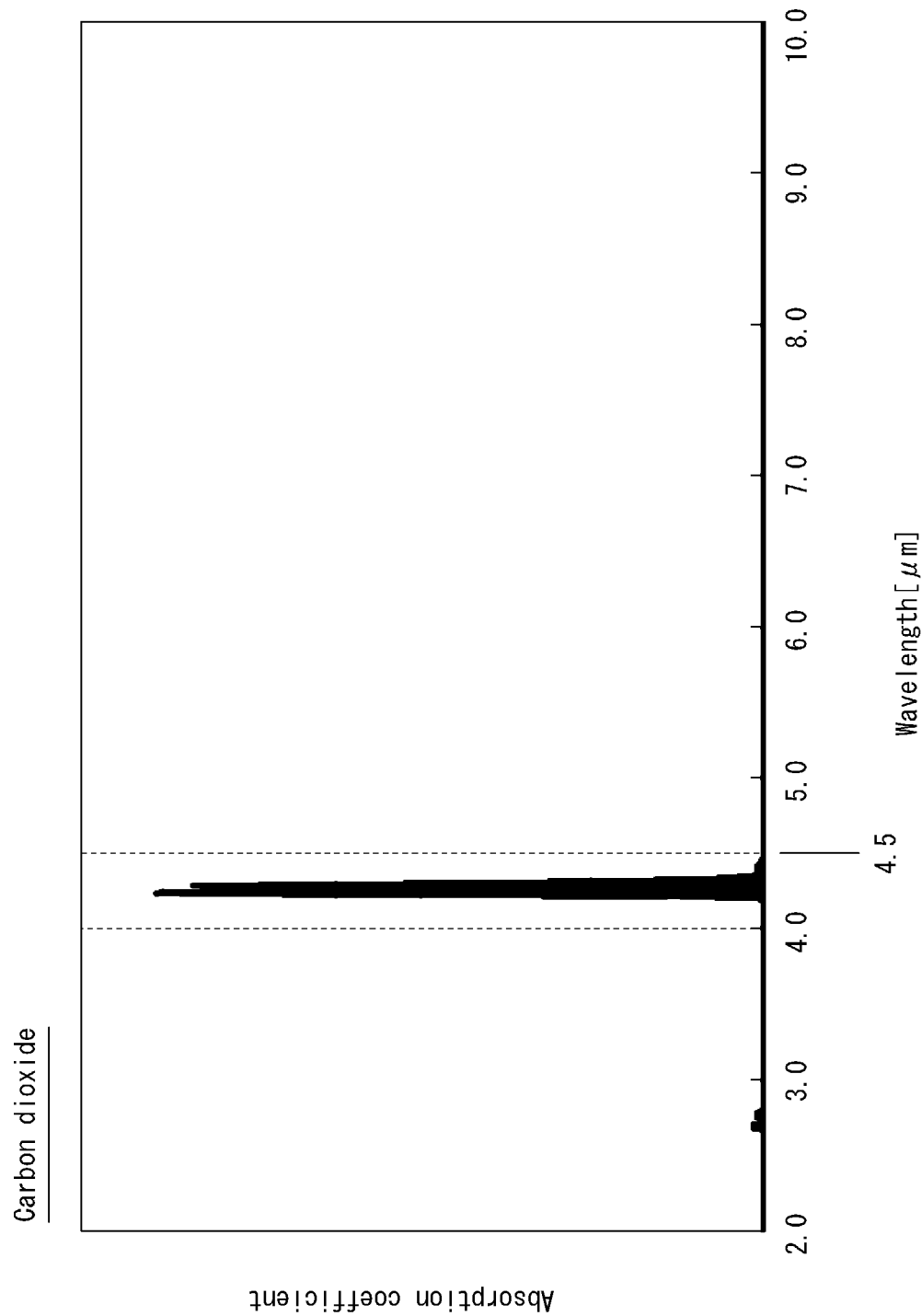

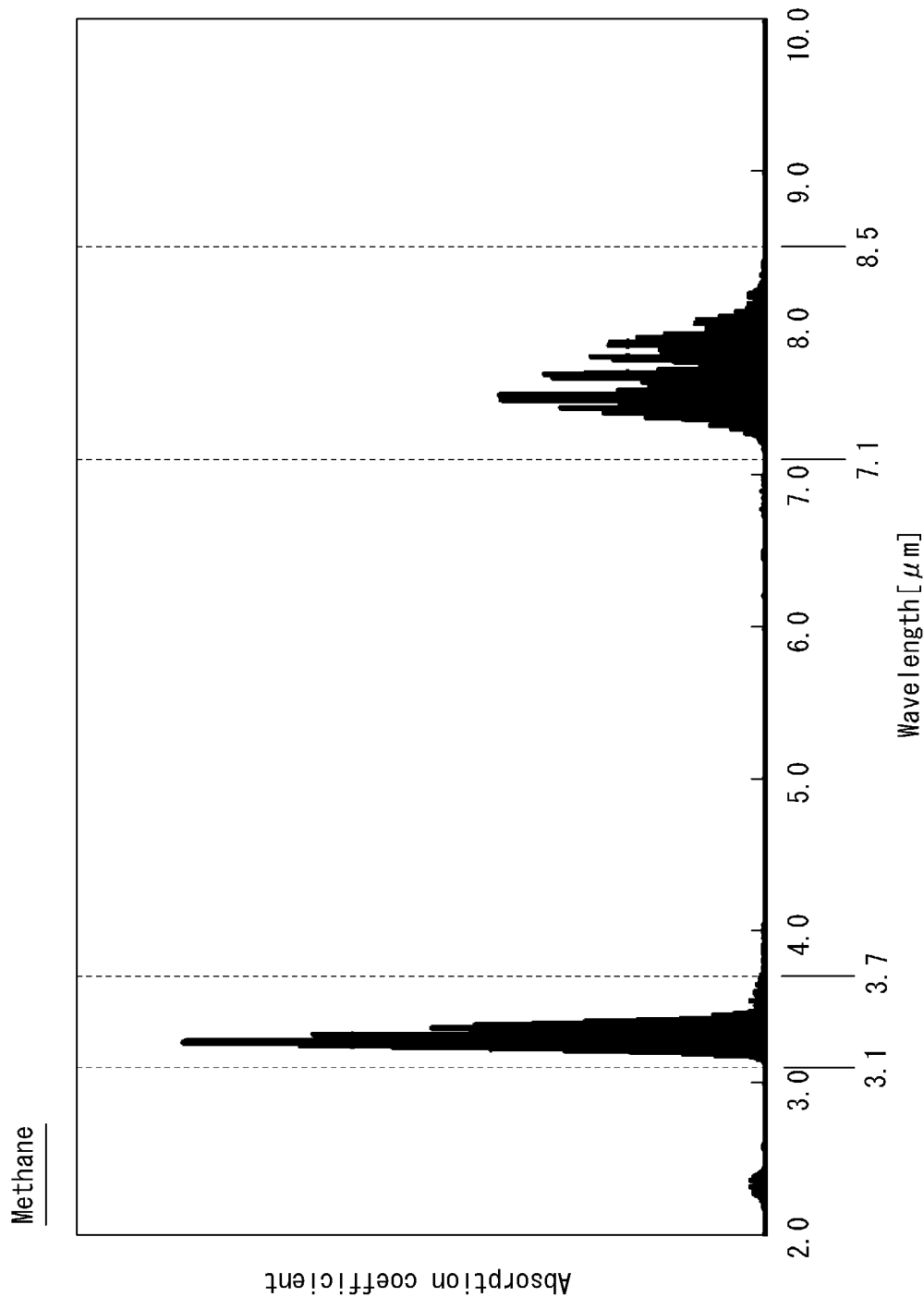

OPTICAL CONCENTRATION MEASURING DEVICE, MODULE FOR OPTICAL CONCENTRATION MEASURING DEVICE AND OPTICAL CONCENTRATION MEASURING METHOD

TECHNICAL FIELD

The present invention relates to an optical concentration measuring device, a module for optical concentration measuring device and an optical concentration measuring method.

BACKGROUND

Optical concentration measurement devices that measure the concentration of a gas to be measured contained in a mixture of the gas to be measured and an interference gas using a light source with a wide spectral width such as a tungsten lamp, instead of a laser light source, and realize low power consumption are known.

For example, Patent Literature 1 (PTL 1) discloses a sensor that includes a light source configured to emit infrared light, a first light receiving part that has a filter having a transmission band that is a wavelength band in which only a gas to be measured absorbs infrared light and a second light receiving part that has a filter having a transmission band that is a wavelength band different from the wavelength band for the first light receiving part, and thus measures the concentration of the gas to be measured while removing the effect of absorption of infrared light by the interference gas.

For example, Patent Literature 2 (PTL 2) discloses a gas concentration measuring device that includes a light source configured to emit infrared light, a first filter configured to transmit infrared light in the absorption band of a gas to be measured and a second filter configured to transmit infrared light in the non-absorption band of a gas to be measured, a rotating member configured to selectively rotate each filter, and a light receiving part configured to receive infrared light transmitted through each filter, and thus achieves miniaturization.

CITATION LIST

Patent Literature

PTL 1: JP2004-138499 A
PTL 2: WO2016/002468 A1

SUMMARY

However, in the known optical concentration measuring devices, in order to avoid the effect of absorption of infrared light by the interference gas, an optical filter having a transmission band that is a wavelength band in which only the gas to be measured absorbs infrared light is used. Thus, when the wavelength band in which only the gas to be measured absorbs infrared light is narrow, the amount of light received by the light receiving part is extremely cut down, and the measuring accuracy of the optical concentration measuring device deteriorates.

It is thus helpful to provide an optical concentration measuring device that can measure the concentration of gas to be measured with high accuracy while removing the effect of light absorption by the interference gas, a module for the optical concentration measuring device and an optical concentration measuring method.

An optical concentration measuring device according to an embodiment is an optical concentration measuring device configured to measure the concentration of a gas to be measured contained in a mixture of the gas to be measured and an interference gas, the device including: a first light source configured to emit infrared light; a first optical filter having a first transmission band that is a wavelength band including a wavelength at which the gas to be measured and the interference gas absorb the infrared light; a first light receiving part that has a sensitivity in the first transmission band and outputs a first detection signal according to a first intensity of light received; a first light guide part configured to guide the infrared light to the first light receiving part; a second light source configured to emit the infrared light; a second optical filter having a second transmission band that is a wavelength band including a wavelength at which the gas to be measured and the interference gas absorb the infrared light; a second light receiving part that has a sensitivity in the second transmission band and outputs a second detection signal according to a second intensity of light received; a second light guide part configured to guide the infrared light to the second light receiving part; and an operation part configured to calculate a first attenuation amount of the first intensity by the gas to be measured and the interference gas based on the first detection signal, a second attenuation amount of the second intensity by the gas to be measured and the interference gas based on the second detection signal, and the concentration of the gas to be measured based on the first attenuation amount and the second attenuation amount, wherein a difference between a peak wavelength of a first effective sensitivity spectrum based on the first transmission band in the first light receiving part and a peak wavelength of a second effective sensitivity spectrum based on the second transmission band in the second light receiving part is ±0.2 times or more and ±0.8 times or less of a full width at half maximum of the first effective sensitivity spectrum, wherein the operation part subtracts the second attenuation amount from an amount obtained by multiplying the first attenuation amount by a proportional constant or subtracts the first attenuation amount from an amount obtained by multiplying the second attenuation amount by a proportional constant different from the above proportional constant to remove an attenuation amount of the first intensity by the interference gas and an attenuation amount of the second intensity by the interference gas.

A module for optical concentration measuring device according to an embodiment is a module for optical concentration measuring device configured to measure the concentration of a gas to be measured contained in a mixture of the gas to be measured and an interference gas, the module including: a first light source configured to emit infrared light; a first optical filter having a first transmission band that is a wavelength band including a wavelength at which the gas to be measured and the interference gas absorb the infrared light; a first light receiving part that has a sensitivity in the first transmission band and receives light transmitted through the first optical filter; a first light guide part configured to guide the infrared light to the first light receiving part; a second light source configured to emit the infrared light; a second optical filter having a second transmission band that is a wavelength band including a wavelength at which the gas to be measured and the interference gas absorb the infrared light; a second light receiving part that has a sensitivity in the second transmission band and receives light transmitted through the second optical filter; and a second light guide part configured to guide the infrared light to the second light receiving part, wherein a difference between a peak wavelength of a first effective sensitivity spectrum based on the first transmission band in the first light receiving part and a peak wavelength of a second effective sensitivity spectrum based on the second transmission band in the second light receiving part is ±0.2 times or more and ±0.8 times or less of a full width at half maximum of the first effective sensitivity spectrum.

An optical concentration measuring method according to an embodiment is an optical concentration measuring method of an optical concentration measuring device configured to measure the concentration of a gas to be measured contained in a mixture of the gas to be measured and an interference gas, the optical concentration measuring device including: a first light source configured to emit infrared light; a first optical filter having a first transmission band that is a wavelength band including a wavelength at which the gas to be measured and the interference gas absorb the infrared light; a first light receiving part that has a sensitivity in the first transmission band and outputs a first detection signal according to a first intensity of light received; a first light guide part configured to guide the infrared light to the first light receiving part; a second light source configured to emit the infrared light; a second optical filter having a second transmission band that is a wavelength band including a wavelength at which the gas to be measured and the interference gas absorb the infrared light; a second light receiving part that has a sensitivity in the second transmission band and outputs a second detection signal according to a second intensity of light received; a second light guide part configured to guide the infrared light to the second light receiving part; and an operation part, wherein a difference between a peak wavelength of a first effective sensitivity spectrum based on the first transmission band in the first light receiving part and a peak wavelength of a second effective sensitivity spectrum based on the second transmission band in the second light receiving part is ±0.2 times or more and ±0.8 times or less of full width at half maximum of the first effective sensitivity spectrum; and the method including the steps of: calculating, by the operation part, a first attenuation amount of the first intensity by the gas to be measured and the interference gas based on the first detection signal; calculating, by the operation part, a second attenuation amount of the second intensity by the gas to be measured and the interference gas based on the second detection signal; and calculating, by the operation part, the concentration of the gas to be measured based on the first attenuation amount and the second attenuation amount, wherein the step of calculating concentration of the gas to be measured includes the step of subtracting, by the operation part, the second attenuation amount from an amount obtained by multiplying the first attenuation amount by a proportional constant, or the first attenuation amount from an amount obtained by multiplying the second attenuation amount by a proportional constant different from the above proportional constant to remove an attenuation amount of the first intensity by the interference gas and an attenuation amount of the second intensity by the interference gas.

According to the present invention, an optical concentration measuring device that can measure the concentration of the gas to be measured with high accuracy while removing the effect of light absorption by the interference gas, a module for the optical concentration measuring device and an optical concentration measuring method can be provided.

BRIEF DESCRIPTION OF THE DRAWINGS

In the accompanying drawings:

FIG. 3A is a diagram illustrating an example of the relationship between the wavelength and the absorption coefficient when carbon dioxide absorbs infrared light;

FIG. 3B is a diagram illustrating an example of the relationship between the wavelength and the absorption coefficient when methane gas absorbs infrared light;

DETAILED DESCRIPTION

Figure 1:
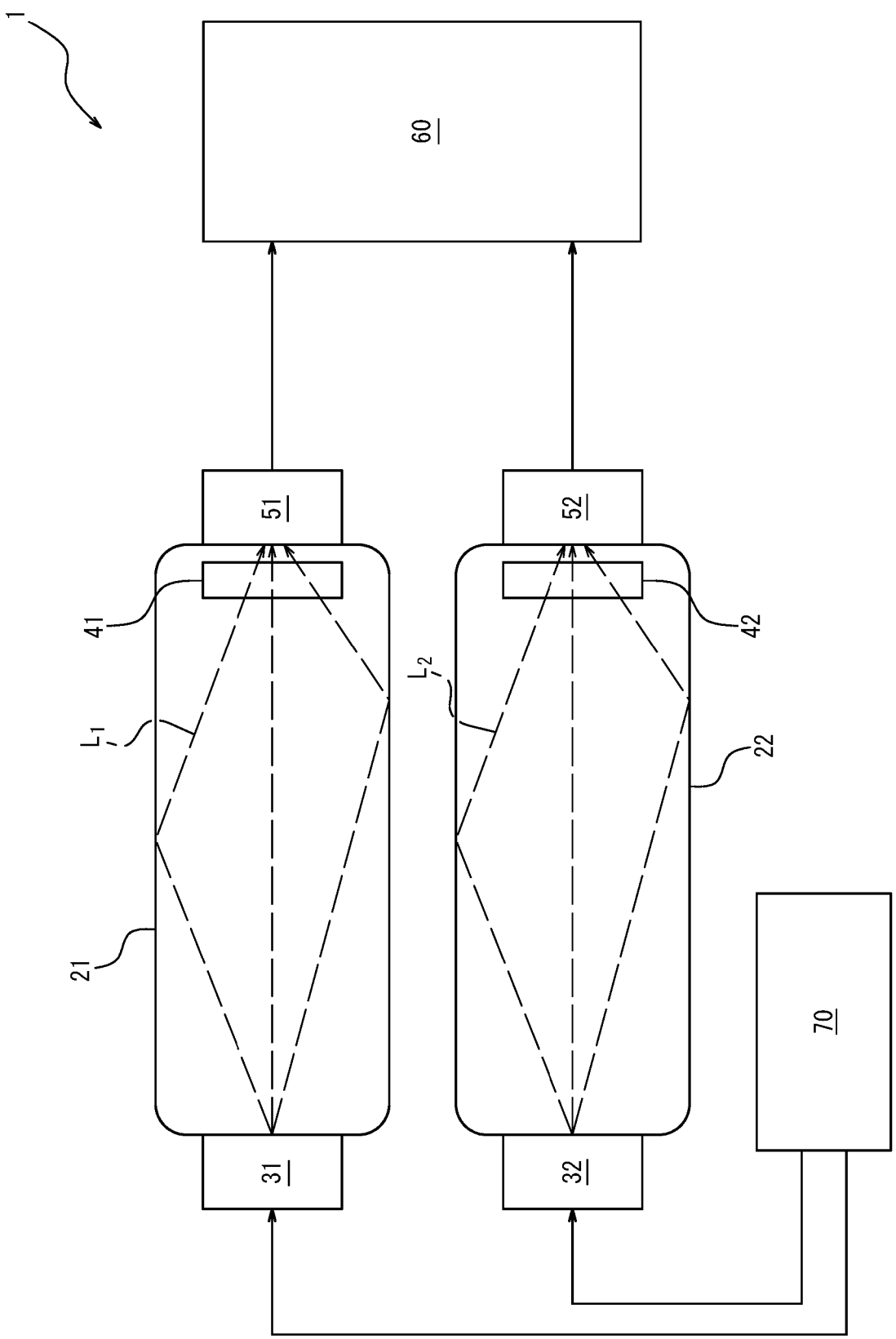
FIG. 1 is a schematic diagram illustrating an example of a configuration of an optical concentration measuring device according to an embodiment of the present invention.
Figure 2:
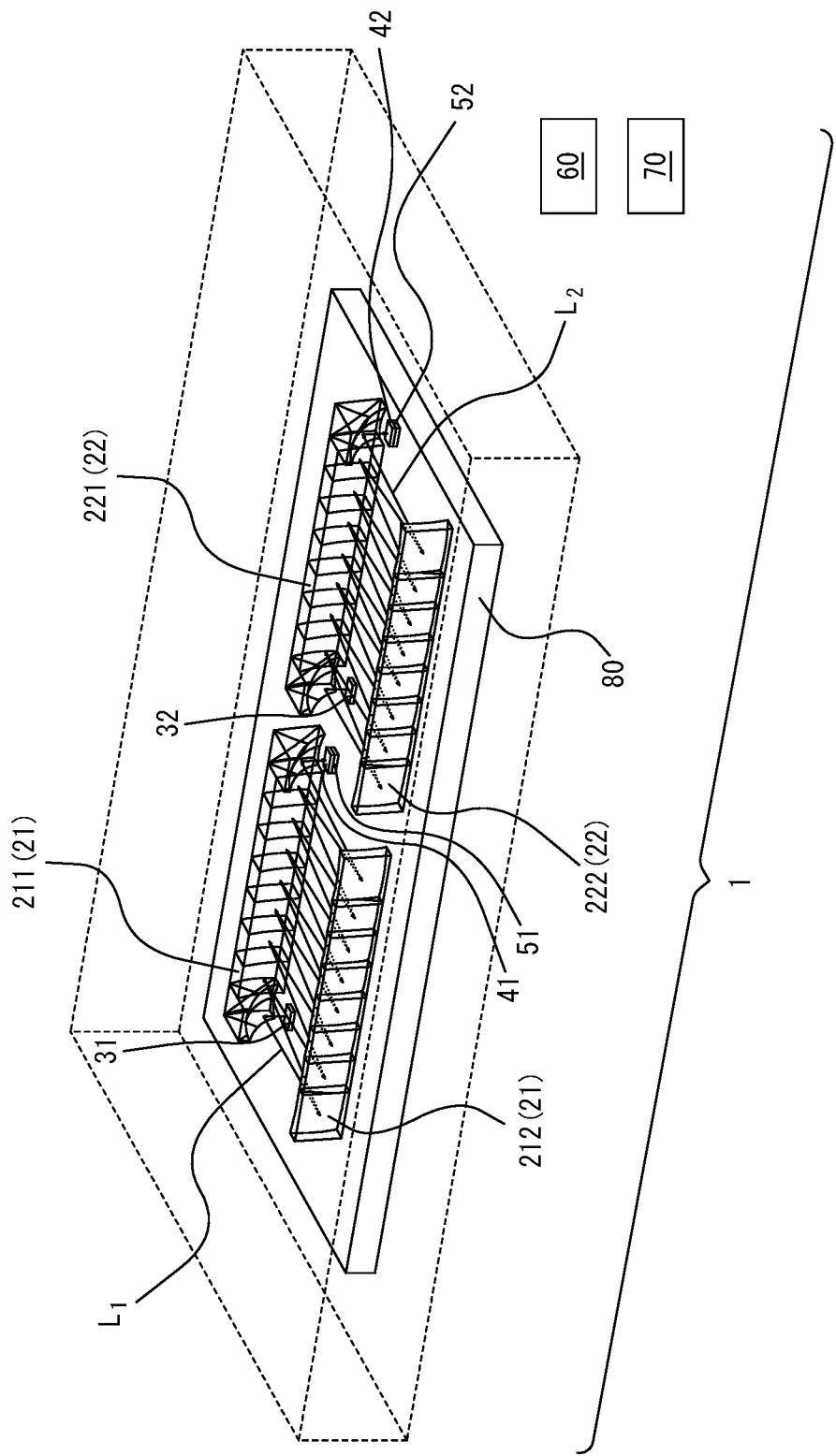
FIG. 2 is a partially transparent perspective view illustrating an example of the configuration of the optical concentration measuring device according to an embodiment of the present invention.

An embodiment of the present invention will be described in detail below with reference to the drawings. In principle, the same reference numbers are assigned to the same components to omit duplicate explanations. In each figure, for convenience of explanation, the aspect ratio of each configuration is exaggerated from the actual ratio.

Hereinafter, the "infrared light" means electromagnetic waves with wavelengths ranging from 2.0 μm to 10.0 μm. Further, the "transmission" means that the amount of light transmitted through the optical filter is 3% or more of the amount of light incident on the optical filter. Further, the "sensitivity" means that the light receiving part absorbs light in a predetermined wavelength band and outputs a current signal or a voltage signal. Further, the "light receiving sensitivity band" means a wavelength band that includes wavelengths of ±50 nm or more and ±500 nm or less from the central wavelength, when the most sensitive wavelength is the central wavelength among the wavelength bands to which the light receiving part is sensitive. However, these terms are defined only for convenience and should not be construed in a limited manner.

<Optical Concentration Measuring Device>

An example of a configuration of an optical concentration measuring device 1 according to the present embodiment will be described with reference to FIGS. 1-6.

The optical concentration measuring device 1 is a non-dispersive infrared (NDIR) type device configured to measure the concentration of a gas to be measured contained in a mixture of the gas to be measured and an interference gas by utilizing the fact that the wavelength of infrared light absorbed differs depending on the type of gas.

Examples of the gas to be measured include, for example, carbon dioxide, methane, water vapor, propane, formaldehyde, carbon monoxide, nitric oxide, ammonia, sulfur dioxide, alcohol, alternative freon, and the like.

The interfering gas is a gas other than the gas to be measured, and examples include carbon dioxide, methane, water vapor, propane, formaldehyde, carbon monoxide, nitric oxide, ammonia, sulfur dioxide, alcohol, alternative freon, and the like. One or more interference gases may be used.

For example, the optical concentration measuring device 1 measures the concentration of carbon dioxide indoors or outdoors. For example, the optical concentration measuring device 1 measures the concentration of methane in order to detect leakage of natural gas in a pipeline that transports natural gas containing methane, which is present only about 2.0 ppm in nature, as a main component.

The optical concentration measuring device 1 includes a first light guide part 21, a second light guide part 22, a first light source 31, a second light source 32, a first optical filter 41, a second optical filter 42, a first light receiving part 51, a second light receiving part 52, an operation part 60, a drive part 70 and a substrate 80.

[First Light Source]

The first light source 31 is preferably an incoherent light source, and is, for example, a Light Emitting Diode (LED), an organic light emitting element, a Micro Electro Mechanical Systems (MEMS) heater, or the like. The first light source 31 emits infrared light based on a drive current or a drive voltage supplied from the drive part 70. The first optical path $L_1$ is an infrared light path through which the infrared light emitted from the first light source 31 is guided to the first light receiving part 51 via the first light guide part 21 in a space in which the gas to be measured and the interference gas are present. The first optical path length $l_1$ is an average optical distance of the path.

The first light source 31 may be integrated into the second light source 32. When the first light source 31 is integrated into the second light source 32, the first light guide part 21 and the second light guide part 22 should be configured so that the infrared light emitted from the light source is taken to each light guide part. In this case, it is necessary that the light amount of either the first light source 31 or the second light source 32 is sufficiently large.

[Second Light Source]

The second light source 32 is preferably an incoherent light source, and is, for example, a Light Emitting Diode (LED), an organic light emitting element, a Micro Electro Mechanical Systems (MEMS) heater, or the like. The second light source 32 emits infrared light based on a drive current or a drive voltage supplied from the drive part 70. The second optical path $L_2$ is an infrared light path through which the infrared light emitted from the second light source 32 is guided to the second light receiving part 52 via the second light guide part 22 in a space in which the gas to be measured and the interference gas are present. The second optical path length $l_2$ is an average optical distance of the path.

The second light source 32 may be integrated into the first light source 31. When the second light source 32 is integrated into the first light source 31, the first light guide part 21 and the second light guide part 22 should be configured so that the infrared light emitted from the light source is taken to each light guide part. In this case, it is necessary that the light amount of either the first light source 31 or the second light source 32 is sufficiently large.

It is preferable that the manufacturing material and the manufacturing process of the second light source 32 are the same as those of the first light source 31. In particular, when the first light source 31 is an LED composed of a semiconductor or a compound semiconductor, the wavelength of the infrared light emitted from the first light source 31 is easily affected by the temperature characteristics due to the band gap. Therefore, from the viewpoint of unifying the temperature characteristics, it is preferable that the second light source 32 is also an LED and identical to the first light source 31.

[First Optical Filter]

The first optical filter 41 transmits the light in the first transmission band. The first transmission band is a wavelength band that includes a wavelength at which the gas to be measured and the interference gas absorb infrared light.

Figure 3C:
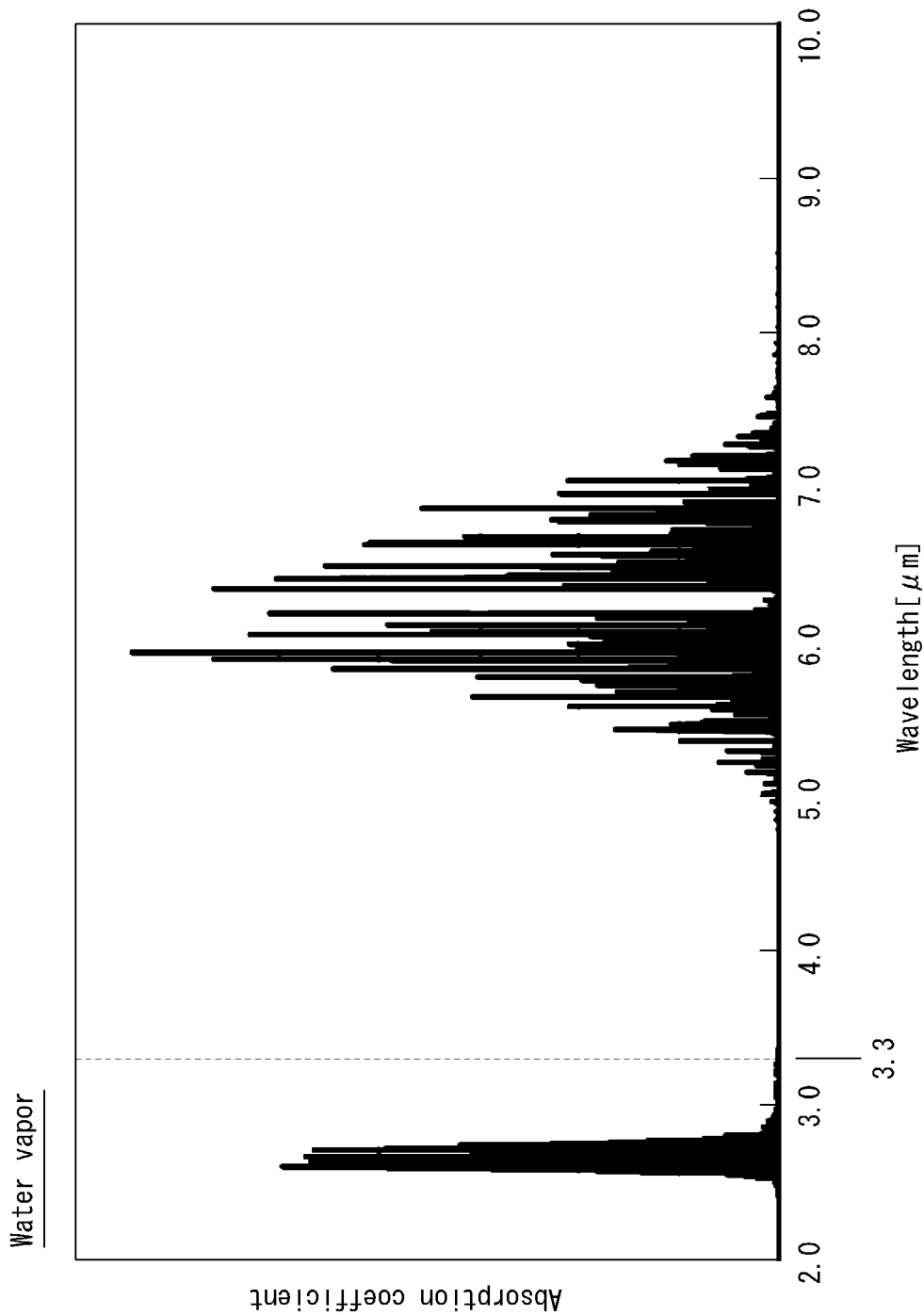
FIG. 3C is a diagram illustrating an example of the relationship between the wavelength and the absorption coefficient when water vapor absorbs infrared light.

As illustrated in FIG. 3A, for example, carbon dioxide mainly absorbs infrared light in a wavelength band from 4.0 µm to 4.5 µm. As illustrated in FIG. 3B, for example, methane mainly absorbs infrared light having a wavelength band from 3.1 µm to 3.7 µm and infrared light having a wavelength band from 7.1 µm to 8.5 µm. This wavelength band is determined based on the molecular vibrational mode of methane. As illustrated in FIG. 3C, for example, water vapor mainly absorbs infrared light having a wavelength band from 2.5 µm to 3.0 µm and infrared light having a wavelength band from 5.0 µm to 8.0 µm.

For example, when the gas to be measured is carbon dioxide and the interference gas is water vapor, the central wavelength of the first transmission band in the first optical filter 41 is preferably from wavelength of 4.0 µm or more to 4.5 µm or less (see FIGS. 3A and 3C).

For example, when the gas to be measured is methane and the interference gas is water vapor, the central wavelength of the first transmission band in the first optical filter 41 is preferably the wavelength of 3.2 µm or more and 3.4 µm or less (see FIGS. 3B and 3C). It is to be noted that, when the wavelength band is the wavelength from 7.1 µm or more to 8.5 µm or less, there is a large overlap between the wavelength band in which methane absorbs infrared light and the wavelength band in which water vapor absorbs infrared light. Thus it is preferable that the first transmission band is within the above described range.

Further, the full width at half maximum of the transmission spectrum of the light transmitted through the first optical filter 41 is preferably 80 nm or more and 300 nm or less. The wider the full width at half maximum, the more wavelengths at which the gas to be measured absorbs infrared light can be taken, and thus the more attenuation of infrared light can be generated. However, in contrast, if the light in an unnecessarily wide wavelength range is taken, the amount of light irrelevant to absorption of infrared light also increases, and as a result, the attenuation rate of infrared light is relatively reduced. Therefore, the full width at half maximum is preferably in the above described range.

[Second Optical Filter]

The second optical filter 42 transmits light in the second transmission band. The second transmission band is a wavelength band that includes a wavelength at which the gas to be measured and the interference gas absorb infrared light.

The full width at half maximum of the transmission spectrum of the light transmitted through the second optical filter 42 is preferably 80 nm or more and 300 nm or less. The wider the full width at half maximum, the more wavelengths at which the gas to be measured absorbs infrared light can be taken, thus more attenuation of infrared light can be generated. However, in contrast, if the light in an unnecessarily wide wavelength range is taken, the amount of light irrelevant to absorption of infrared light also increases, and as a result, the attenuation rate of infrared light is relatively reduced. Therefore, the full width at half maximum is preferably in the above described range.

When the first light receiving part 51 and the second light receiving part 52 have the same configuration, it is preferable that the second optical filter 42 has a configuration different from that of the first optical filter 41.

[First Light Receiving Part]

The first light receiving part 51 is, for example, a photodiode, a phototransistor, or the like. The first light receiving part 51 is sensitive to the first transmission band and receives light transmitted through the first optical filter 41. The first light receiving sensitivity band in the first light receiving part 51 is preferably optimized with respect to the first transmission band. Further, the first light receiving sensitivity band preferably includes the first transmission band. When the first light receiving sensitivity band includes the first transmission band, the first light receiving part 51 can receive the light transmitted through the first optical filter 41 with high efficiency.

The first light receiving part 51 generates a first detection signal according to the first intensity of the light received and outputs the signal to the operation part 60. The first detection signal is a current signal or a voltage signal. A first attenuation amount described later is calculated by the operation part 60 based on the first detection signal.

For example, when the gas to be measured and the interference gas are present in the first optical path $L_1$, the first light receiving part 51 outputs a first detection signal according to the first intensity of the light received to the operation part 60. Further, for example, the first light receiving part 51 outputs a first detection signal according to the first intensity of the light received to the operation part 60 when the gas to be measured and the interference gas are not present in the first optical path $L_1$. The first attenuation amount is an amount calculated by the operation part 60 based on a difference between a first detection signal output from the first light receiving part 51 when the gas to be measured and the interference gas are not present in the first optical path $L_1$ and a first detection signal output from the first light receiving part 51 when the gas to be measured and the interference gas are present in the first optical path $L_1$. It is to be noted that it is difficult for the first light receiving part 51 to detect a first detection signal when the gas to be measured and the interference gas are not present in the first optical path $L_1$ under the actual use environment. Therefore, a first detection signal when the gas to be measured and the interference gas are not present in the first optical path $L_1$ may be set in advance and stored in the operation part 60, or may be calculated by the operation part 60 based on the environment information such as ambient temperatures.

[Second Light Receiving Part]

The second light receiving part 52 is, for example, a photodiode, a phototransistor, or the like. The second light receiving part 52 is sensitive to the second transmission band and receives light transmitted through the second optical filter 42. The second light receiving sensitivity band in the second light receiving part 52 is preferably optimized with respect to the second transmission band. Further, the second light receiving sensitivity band preferably includes a second transmission band. When the second light receiving sensitivity band includes the second transmission band, the second light receiving part 52 can receive the light transmitted through the second optical filter 42 with high efficiency.

The second light receiving sensitivity band is different from the first light receiving sensitivity band, and may be optimized to the second transmission band, but when the first transmission band and the second transmission band are different from each other, the second light receiving sensitivity band may be identical to the first light receiving sensitivity band.

The second light receiving part 52 generates a second detection signal according to the second intensity of the light received and outputs the signal to the operation part 60. The second detection signal is a current signal or a voltage signal. A second attenuation amount described later is calculated by the operation part 60 based on the second detection signal.

For example, when the gas to be measured and the interference gas are present in the second optical path $L_2$, the second light receiving part 52 outputs a second detection signal according to the second intensity of the light received to the operation part 60. Further, for example, the second light receiving part 52 outputs a second detection signal according to the second intensity of the light received to the operation part 60 when the gas to be measured and the interference gas are not present in the second optical path $L_2$. The second attenuation amount is an amount calculated by the operation part 60 based on a difference between a second detection signal output from the second light receiving part 52 when the gas to be measured and the interference gas are not present in the second optical path $L_2$ and a second detection signal output from the second light receiving part 52 when the gas to be measured and the interference gas are present in the second optical path $L_2$. It is to be noted that it is difficult for the second light receiving part 52 to detect a second detection signal when the gas to be measured and the interference gas are not present in the second optical path $L_2$ under the actual use environment. Therefore, a second detection signal when the gas to be measured and the interference gas are not present in the second optical path $L_2$ may be set in advance and stored in the operation part 60, or may be calculated by the operation part 60 based on the environment information such as ambient temperatures.

It is preferable that the manufacturing material and the manufacturing process of the second light receiving part 52 are the same as those of the first light receiving part 51. In particular, when the first light receiving part 51 is a photodiode or a phototransistor composed of a semiconductor or a compound semiconductor, the first light receiving sensitivity band of the first light receiving part 51 is easily affected by the temperature characteristics. Therefore, from the viewpoint of unifying the temperature characteristics, it is preferable that the second light receiving part 52 is also a photodiode or a phototransistor, which is identical to the first light receiving part 31.

It is to be noted that the first light receiving part 51 does not detect infrared light, in a wavelength band other than the first transmission band, emitted from those containing heat such as processors. Similarly, the second light receiving part 52 does not detect infrared light, in a wavelength band other than the second transmission band, emitted from those containing heat such as processors. Therefore, it is preferable that the first light receiving part 51 and the second light receiving part 52 are each provided with an optical filter directly above.

[Effective Sensitivity Spectrum]

Here, the first effective sensitivity spectrum and the second effective sensitivity spectrum will be described with reference to FIG. 4. The horizontal axis represents the wavelength [μm] and the vertical axis represents the intensity ratio of the effective sensitivity spectrum [a.u.]. Further, the solid line represents the first effective sensitivity spectrum, and the dashed line and dashed-dotted line represent the second effective sensitivity spectrum.

The first effective sensitivity spectrum of the first light receiving part 51 is a spectrum of light in a wavelength band in which the first light receiving part 51 has an effective sensitivity, and is defined as a spectrum obtained by multiplying the first transmission band in the first optical filter 41 and the spectrum of the light in the first light receiving sensitivity band in the first light receiving part 51. In other words, it can be said that the characteristics of the first effective sensitivity spectrum of the first light receiving part 51 are generally determined based on the first transmission band.

The second effective sensitivity spectrum of the second light receiving part 52 is a spectrum of light in the wavelength band in which the second light receiving part 52 has an effective sensitivity, and is defined as a spectrum obtained by multiplying the second transmission band in the second optical filter 42 and the spectrum of the light in the second light receiving sensitivity band in the second light receiving part 52. In other words, it can be said that the characteristics of the second effective sensitivity spectrum of the second light receiving part 52 are generally determined based on the second transmission band.

The full width at half maximum of the first effective sensitivity spectrum is preferably 80 nm or more and 300 nm or less. Similarly, the full width at half maximum of the second effective sensitivity spectrum is preferably 80 nm or more and 300 nm or less. The wider the full width at half maximum of each effective sensitivity spectrum, the more the wavelength at which a gas to be measured absorbs the infrared light can be taken, and a lot of attenuation amount of infrared light can be caused. In contrast, if the light in an unnecessarily wide wavelength range is taken, the amount of light irrelevant to the absorption of infrared light also increases, and thus the attenuation rate of infrared light is relatively reduced. Therefore, the full width at half maximum of the first effective sensitivity spectrum and that of the second effective sensitivity spectrum are preferably in the above described ranges.

Figure 4:
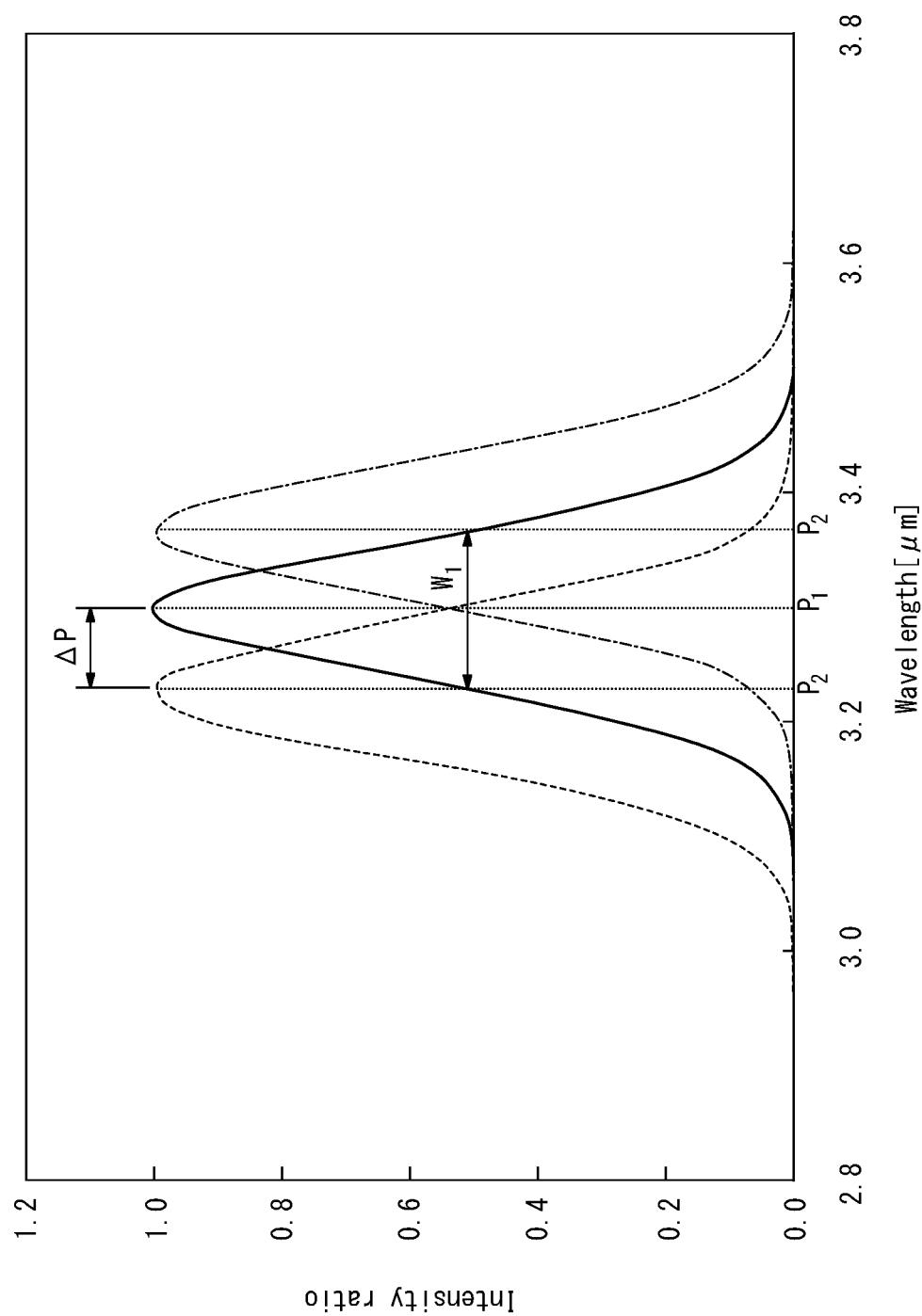
FIG. 4 is a diagram illustrating an example of the relationship between the wavelength and the intensity ratio of the effective sensitivity spectrum in the first effective sensitivity spectrum and the second effective sensitivity spectrum according to an embodiment of the present invention.

As illustrated in FIG. 4, the difference ΔP between the peak wavelength $P_1$ of the first effective sensitivity spectrum and the peak wavelength $P_2$ of the second effective sensitivity spectrum is preferably 0.2 times or more and 0.8 times or less the full width at half maximum $W_1$ of the first effective sensitivity spectrum. In other words, the peak wavelength $P_2$ of the second effective sensitivity spectrum is preferably a wavelength obtained as a result of peak shift from the peak wavelength $P_1$ of the first effective sensitivity spectrum to the low energy side by 0.2 times or more and 0.8 times or less the full width at half maximum $W_1$ of the first effective sensitivity spectrum. Alternatively, the peak wavelength $P_2$ of the second effective sensitivity spectrum is preferably a wavelength obtained as a result of peak shift from the peak wavelength $P_1$ of the first effective sensitivity spectrum to the high energy side by 0.2 times or more and 0.8 times or less the full width at half maximum $W_1$ of the first effective sensitivity spectrum.

For example, when the peak wavelength $P_1$ of the first effective sensitivity spectrum is 3.3 μm and the full width at half maximum $W_1$ of the first effective sensitivity spectrum is 140 nm, it is preferable that the peak wavelength $P_2$ of the second effective sensitivity spectrum is 3.23 μm (=3.3 μm−0.07 μm), which is a wavelength obtained as a result of peak shift to the high energy side by 0.5 times (=70 nm) the full width at half maximum $W_1$ 140 nm of the first effective sensitivity spectrum. Alternatively, it is 3.37 μm (=3.3 μm+0.07 μm), which is a wavelength obtained as a result of peak shift to the low energy side by 0.5 times (=70 nm) the full width at half maximum $W_1$ 140 nm of the first effective sensitivity spectrum.

When the difference ΔP between the peak wavelength $P_1$ of the first effective sensitivity spectrum and the peak wavelength $P_2$ of the second effective sensitivity spectrum is 0.2 times or more and 0.8 times or less the full width at half maximum $W_1$ of the first effective sensitivity spectrum, in order to avoid effect of absorption of infrared light by the interference gas, the optical concentration measuring device 1 does not need to be provided with an optical filter having a transmission band that is a wavelength band in which only the gas to be measured absorbs infrared light, as with the known optical concentration measuring devices. Therefore, even if the wavelength band in which the gas to be measured absorbs infrared light is narrow, the light receiving part can receive a sufficient amount of light, and thus the optical concentration measuring device 1 capable of performing highly reliable measurement can be realized.

Further, when the difference ΔP between the peak wavelength $P_1$ of the first effective sensitivity spectrum and the peak wavelength $P_2$ of the second effective sensitivity spectrum is 0.2 times or more and 0.8 times or less the full width at half maximum $W_1$ of the first effective sensitivity spectrum, the structures or compositions of the first optical filter 41 and the second optical filter 42 can be brought close to each other. Thus, improvement of the temperature characteristics can be expected.

Here, the reason why improvement in temperature characteristics can be expected will be described.

In the known optical concentration measuring devices, for example, a light receiving part that has a first optical filter having a transmission band that is a wavelength band in which the gas to be measured and the interference gas absorb infrared light and a light receiving part that has a second optical filter having a transmission band that is a wavelength band in which only the interference gas absorbs infrared light are provided so as to completely separate the transmission bands of two optical filters from each other, and the effect of absorption of infrared light by the interference gas is eliminated. Therefore, it is difficult to bring the structures and the compositions of the first optical filter and the second optical filter close to each other, and differences occur between temperature characteristics of the two optical filters. The differences also deteriorate the measuring accuracy of the optical concentration measuring device.

However, in the optical concentration measuring device 1 according to the present embodiment, the effect of the infrared light absorption by the interference gas can be eliminated by using two optical filters having transmission bands close to each other, and further, by applying the interference removal calculation by the operation part 60 described in detail below, without completely separating transmission bands of two optical filters, as in the known optical concentration measuring devices. In other words, since it is not necessary to completely separate the transmission bands of two optical filters, and the structures or the compositions of the first optical filter 41 and the second optical filter 42 can be brought close to each other, it is possible to make a difference between temperature characteristics of the first optical filter 41 and the second optical filter 42 unlikely to occur. Therefore, the optical concentration measuring device 1 that avoids deterioration of measurement accuracy caused by a difference in temperature characteristics can be realized.

Further, the wider the overlapping area of the first effective sensitivity spectrum and the second effective sensitivity spectrum, the closer the first transmission band, the first light receiving sensitivity band, the second transmission band and the second light receiving sensitivity band. Therefore, in the optical concentration measuring device 1, the structures or the compositions of the first optical filter 41 and the second optical filter 42, those of the first light source 31 and the second light source 32, and those of the first light receiving part 51 and the second light receiving part 52 can be brought close to each other, and further improvement of the temperature characteristics can be expected.

As described above, when the peak shift in the peak wavelength of the second effective sensitivity spectrum with respect to the peak wavelength of the first effective sensitivity spectrum is appropriately adjusted, even if the wavelength band in which the gas to be measured absorbs infrared light is narrow, the optical concentration measuring device 1 capable of measuring the concentration of the gas to be measured with high accuracy can be realized while improving the temperature characteristics, without drastically reducing the amount of light received by the first light receiving part 51 and the second light receiving part 52.

[First Light Guide Part]

The first light guide part 21 guides infrared light emitted from the first light source 31 to the first light receiving part 51. For example, the first light guide part 21 reflects infrared light multiple times or rotationally converts the radiation angle at the time of emitting infrared light so that infrared light emitted from the first light source 31 eventually reaches the first light receiving part 51.

The first light guide part 21 includes a mirror 211 and a mirror 212. The mirrors 211 and 212 are preferably made of the same material, for example, they are preferably made of metal, glass, ceramics, stainless steel, or the like.

From the viewpoint of improving the sensitivity, the mirrors 211 and 212 are preferably made of a material having a small light absorption coefficient and a high reflectance. Examples of such a material include an alloy containing aluminum, gold, and silver, a dielectric, or a resin housing coated with a laminate thereof. Examples of the material of the resin housing include liquid crystal polymer (LCP), polypropylene (PP), polyetheretherketone (PEEK), polyetherketone (PA), polyphenylene ether (PPE), polycarbonate (PC), polyphenylene sulfide (PPS), polymethyl methacrylate resin (PMMA), or a hard resin that is a mixture of two or more of them.

Further, the mirrors 211 and 212 are preferably formed of a resin housing coated with gold or an alloy layer containing gold, from the viewpoint of improving reliability and suppressing deterioration over time. Furthermore, in order to increase the reflectance, it is preferable that a dielectric laminated film is formed on the surface of the metal layer. When the inner surface of the first light guide part 21 is formed by vapor deposition or plating on the resin housing, productivity can be improved, and weight can be reduced.

The first light guide part 21 is not limited to the mirrors 211 and 212, and may be an optical element. For example, the first light guide part 21 may be multiple lenses. For example, the first light guide part 21 may be a combination of multiple mirrors and multiple lenses.

[Second Light Guide Part]

The second light guide part 22 guides infrared light emitted from the second light source 32 to the second light receiving part 52. For example, the second light guide part 22 reflects infrared light multiple times or rotationally converts the radiation angle at the time of emitting infrared light so that infrared light emitted from the second light source 32 eventually reaches the second light receiving part 52.

The second light guide part 22 includes a mirror 221 and a mirror 222. The mirrors 221 and 222 are preferably made of the same material, for example, they are preferably made of metal, glass, ceramics, stainless steel, or the like.

From the viewpoint of improving the sensitivity, the mirrors 221 and 222 are preferably made of a material having a small light absorption coefficient and a high reflectance. Examples of such a material include an alloy containing aluminum, gold, and silver, a dielectric, or a resin housing coated with a laminate thereof. Examples of the material of the resin housing include liquid crystal polymer (LCP), polypropylene (PP), polyetheretherketone (PEEK), polyamide (PA), polyphenylene ether (PPE), polycarbonate (PC), polyphenylene sulfide (PPS), polymethyl methacrylate resin (PMMA), or a hard resin that is a mixture of two or more of them.

Further, the mirrors 221 and 222 are preferably formed of a resin housing coated with gold or an alloy layer containing gold from the viewpoint of improving reliability and suppressing deterioration over time. Furthermore, in order to increase the reflectance, it is preferable that a dielectric laminated film is formed on the surface of the metal layer. When the inner surface of the second light guide part 22 is formed by vapor deposition or plating on the resin housing, productivity can be improved, and weight can be reduced.

The second light guide part 22 is not limited to the mirrors 221 and 222, and may be an optical element. For example, the second light guide part 22 may be a plurality of lenses. For example, the second light guide part 22 may be a combination of a plurality of mirrors and a plurality of lenses.

[Operation Part]

The operation part 60 may include at least one of the drive part 70, a general-purpose processor that executes a function according to a program to be read, and a dedicated processor specialized for a specific process. The dedicated processor may include an application specific IC (ASIC; Application Specific Integrated Circuit) or a non-volatile/volatile memory.

The operation part 60 calculates the first attenuation amount of the first intensity of infrared light by the gas to be measured and the interference gas present in the first optical path $L_1$ based on the first detection signal output from the first light receiving part 51. The first attenuation amount is an amount calculated based on a difference between the first detection signal output from the first light receiving part 51 when gas to be measured and interference gas are not present in the first optical path $L_1$ and the first detection signal output from the first light receiving part 51 when gas to be measured and interference gas are present in the first optical path $L_1$.

Next, the operation part 60 calculates the second attenuation amount of the second intensity of infrared light by the gas to be measured and the interference gas present in the second optical path $L_2$ based on the second detection signal output from the second light receiving part 52. The second attenuation amount is an amount calculated based on a difference between the second detection signal output from the second light receiving part 52 when gas to be measured and interference gas are not present in the first optical path $L_2$ and the second detection signal output from the second light receiving part 51 when gas to be measured and interference gas are present in the second optical path $L_2$.

Next, the operation part 60 calculates the concentration of gas to be measured based on the first attenuation amount and the second attenuation amount. For example, the operation part 60 calculates the concentration of gas to be measured by subtracting the second attenuation amount from the amount obtained by multiplying the first attenuation amount by a proportional constant, and performing an interference removal operation in which the attenuation amount of the first intensity of infrared light by the interference gas present in the first optical path $L_1$ and the attenuation amount of the second intensity of infrared light by the interference gas present in the second optical path $L_2$ are removed. For example, the operation part 60 calculates the concentration of gas to be measured by subtracting the first attenuation amount from the amount obtained by multiplying the second attenuation amount by a proportional constant, and performing an interference removal operation in which the attenuation amount of the first intensity of infrared light by the interference gas present in the first optical path $L_1$ and the attenuation amount of the second intensity of infrared light by the interference gas present in the second optical path $L_2$ are removed.

Here, about the fact that the attenuation amount of the first intensity of infrared light by the interference gas present in the first optical path $L_1$ and the attenuation amount of the second intensity of infrared light by the interference gas present in the second optical path $L_2$ are in a proportional relationship will be described. For example, a description will be given for the case where gas to be measured is methane and interference gas is water vapor.

The attenuation amount $\Delta I$ of the intensity of infrared light by gas is expressed by the following equation (1) according to the Lambert-Beer law.

$$\Delta I = I_0 \{1 - e^{(-ecl)}\} \quad (1),$$

where $I_0$ is the intensity of infrared light in the absence of gas in the optical path, e is a gas-specific absorption coefficient, c is concentration of gas, and l is an optical path length in a range where gas is present.

From equation (1), it is clear that the attenuation amount $\Delta I$ of the intensity of infrared light by gas behaves exponentially. However, when ecl is a value close to 0, the attenuation amount $\Delta I$ of the intensity of infrared light by gas is expressed by the following equation (2) using a polynomial, which is a Maclaurin expansion of the exponential function.

$$\Delta I = I_0 \{1 - e^{(-ecl)}\} \cong I_0 \left\{1 - \left(1 - ecl + \frac{1}{2}(ecl)^2 - \frac{1}{6}(ecl)^3 + ...\right)\right\} \quad (2)$$

In particular, when ecl is a value close to 0, the attenuation amount $\Delta I$ of the intensity of infrared light by gas behaves like a linear function. For example, when the methane concentration of 100 ppm is measured, the concentration of water vapor is about 15,000 ppm in an environment where the temperature is 25° C. and the relative humidity is 50% R. H., so the concentration of water vapor is about 150 times that of methane. However, as illustrated in FIGS. 3B and 3C, when the wavelength is around 3.3 the absorbing coefficient of infrared light by methane is extremely large, but the absorbing coefficient of infrared light by water vapor is extremely small. In other words, the attenuation amount of the intensity of infrared light by water vapor is a linear function with respect to the concentration of water vapor.

Figure 5:
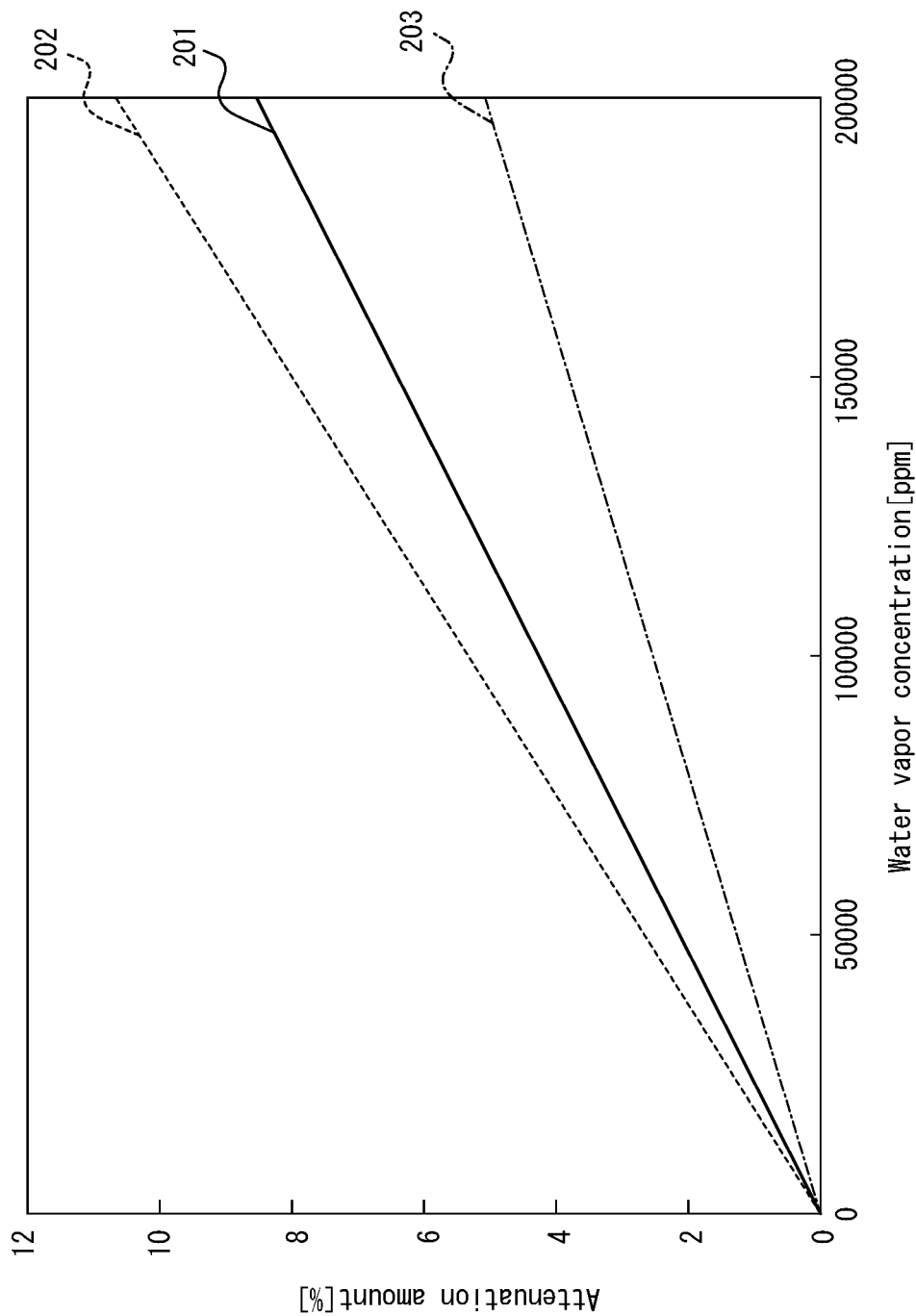
FIG. 5 is a diagram illustrating an example of the relationship between the concentration of water vapor and the attenuation amount of infrared light in the first effective sensitivity spectrum and the second effective sensitivity spectrum according to an embodiment of the present invention.

FIG. 5 illustrates the relationship between the concentration of water vapor and the attenuation amount of the intensity of infrared light by water vapor in the first effective sensitivity spectrum and the second effective sensitivity spectrum. The horizontal axis represents the concentration [ppm] of water vapor and the vertical axis represents the attenuation amount [%] of the intensity of infrared light. In the graph illustrated in FIG. 5, the calculation is made with a spectrum having a peak wavelength $P_1$ of 3.3 μm and a full width at half maximum $W_1$ of 140 nm as a first effective sensitivity spectrum and a spectrum having a peak shift of the peak wavelength $P_2$ with respect to the peak wavelength $P_1$ of ±70 nm as a second effective sensitivity spectrum (see FIG. 4).

The solid line graph 201 illustrates the relationship between the concentration of water vapor and the attenuation amount of the intensity of infrared light by water vapor in the first effective sensitivity spectrum. The dashed-line graph 202 illustrates the relationship between the concentration of water vapor and the attenuation amount of the intensity of infrared light by water vapor in the second effective sensitivity spectrum. The dashed-dotted line graph 203 illustrates the relationship between the concentration of water vapor and the attenuation amount of the intensity of infrared light by water vapor in the second effective sensitivity spectrum.

From FIG. 5, it is clear that the graph 201 is a linear function, and the attenuation amount of the intensity of infrared light by water vapor in the first effective sensitivity spectrum is proportional to the concentration of water vapor. Further, it is clear that the graph 202 is a linear function, and the attenuation amount of the intensity of infrared light by water vapor in the second effective sensitivity spectrum is proportional to the concentration of water vapor. Then, the graph 203 is a linear function, and it is clear that the attenuation amount of the intensity of infrared light by water vapor in the second effective sensitivity spectrum is proportional to the concentration of water vapor.

Further, from FIG. 5, it is clear that the graphs 201, 202 and 203 have slopes of the linear function different from each other. In other words, the slope of each linear function changes as the effective sensitivity spectrum changes. This is because the value of e in the equation (2) changes as the effective sensitivity spectrum changes.

Figure 6:
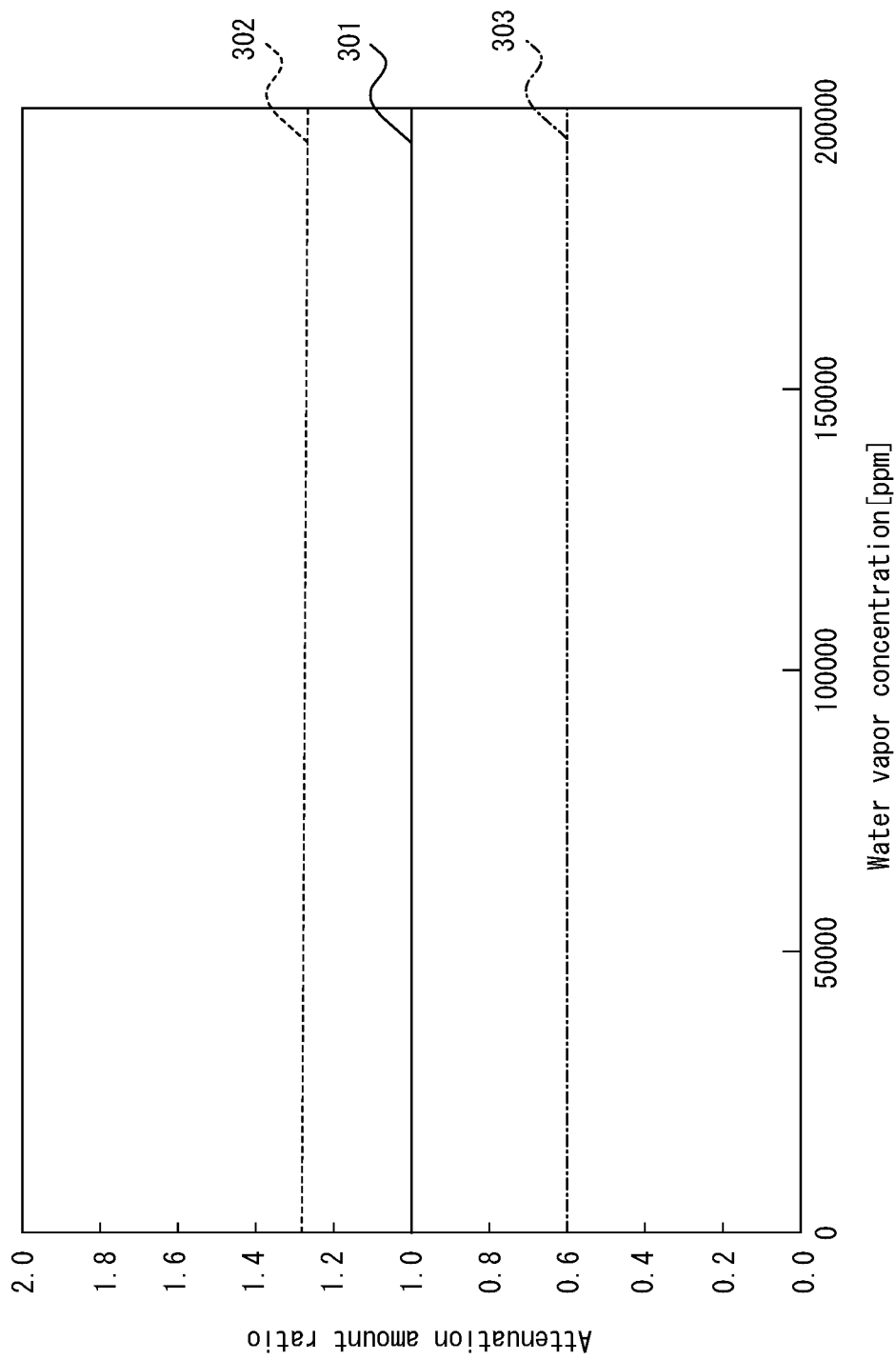
FIG. 6 is a diagram illustrating an example of the relationship between the concentration of water vapor and the attenuation amount ratio of infrared light in the first effective sensitivity spectrum and the second effective sensitivity spectrum according to an embodiment of the present invention.

FIG. 6 illustrates the relationship between the concentration of water vapor and the attenuation amount ratio of the intensity of infrared light by water vapor in the first and second effective sensitivity spectra. The horizontal axis represents the concentration [ppm] of water vapor and the vertical axis represents the attenuation ratio [a.u.] of the intensity of infrared light. As a reference of ratio, the attenuation amount of the intensity of infrared light by the concentration of water vapor in the first effective sensitivity spectrum is used. The graphs illustrated in FIG. 6 are calculated by using a spectrum having a peak wavelength $P_1$ of 3.3 μm and a full width at half maximum $W_1$ of 140 nm as the first effective sensitivity spectrum, and a spectrum having a peak shift of peak wavelength $P_2$ with respect to peak wavelength $P_1$ of ±70 nm as the second effective sensitivity spectrum (see FIG. 4).

The solid line graph 301 illustrates the relationship between the concentration of water vapor and the attenuation amount ratio of the intensity of infrared light by water vapor in the first effective sensitivity spectrum, which is a reference. The dashed line graph 302 illustrates the relationship between the concentration of water vapor and the attenuation amount ratio of the intensity of infrared light by water vapor in the second effective sensitivity spectrum with respect to the relationship between the concentration of water vapor and the attenuation amount of the intensity of infrared light by water vapor in the first effective sensitivity spectrum. The dashed-dotted line graph 303 illustrates the relationship between the concentration of water vapor and the attenuation amount ratio of the intensity of infrared light by water vapor in the second effective sensitivity spectrum with respect to the relationship between the concentration of water vapor and the attenuation amount of the intensity of infrared light by water vapor in the first effective sensitivity spectrum.

From FIG. 6, it is clear that the graph 302 is substantially horizontal and the attenuation amount ratio is maintained at approximately 1.3. It is clear that the graph 303 is substantially horizontal and the attenuation amount ratio is maintained at approximately 0.6. In other words, it is clear that, even if the effective sensitivity spectrum changes, the attenuation amount ratio does not depend on the concentration of water vapor and is substantially constant.

Therefore, from FIGS. 5 and 6, it is clear that the attenuation amount of the first intensity of infrared light by water vapor present in the first optical path $L_1$ and the attenuation amount of the second intensity of infrared light by water vapor present in the second optical path $L_2$ are in a proportional relationship.

As described above, since the attenuation amount of the first intensity of infrared light by interference gas present in the first optical path $L_1$ and the attenuation amount of the second intensity of infrared light by interference gas present in the second optical path $L_2$ are in a proportional relationship, the operation part 60 can remove the attenuation amount of the first intensity of infrared light by interference gas present in the first optical path $L_1$ and the attenuation amount of the second intensity of infrared light by interference gas present in the second optical path $L_2$ by subtracting the second attenuation amount from the amount obtained by multiplying the first attenuation amount by a proportional constant. Alternatively, since the attenuation amount of the first intensity of infrared light by interference gas present in the first optical path $L_1$ and the attenuation amount of the second intensity of infrared light by interference gas present in the second optical path $L_2$ are in a proportional relationship, the operation part 60 can remove the attenuation amount of the first intensity of infrared light by interference gas present in the first optical path $L_1$ and the attenuation amount of the second intensity of infrared light by the interference gas present in the second optical path $L_2$ by subtracting the first attenuation amount from the amount obtained by multiplying the second attenuation amount by a proportional constant.

In general, when the optical concentration measuring device measures the concentration of a gas to be measured contained in a mixture of the gas to be measured and an interference gas, it is extremely difficult to specify how much the infrared light intensity is attenuated by the gas to be measured and how much the infrared light intensity is attenuated by the interference gas. However, as is clear from FIGS. 5 and 6, the attenuation amount of the first intensity of infrared light by the water vapor present in the first optical path $L_1$ and the attenuation amount of the second intensity of infrared light by the water vapor present in the second optical path $L_2$ are in a proportional relationship. Therefore, the operation part 60 can easily remove the effect of absorption of infrared light by water vapor by using the ratio of the slopes of the linear functions illustrated in FIGS. 5 and 6 as proportional constants for calculation.

Therefore, the optical concentration measuring device 1 can remove the effect of absorption of infrared light by the interference gas by performing the interference removal operation by the operation part 60 as described above using two optical filters having transmission bands close to each other, without completely separating the transmission bands of the two optical filters, as with the known optical concentration measuring devices. Thus, even if the wavelength band in which the gas to be measured absorbs infrared light is narrow, the amount of light received by the first light receiving part 51 and the second light receiving part 52 is not cut down drastically, which enables measurement of the concentration of the gas to be measured with high accuracy.

Further, it is preferable that the SNR (Signal to Noise Ratio) is substantially equal between the first attenuation amount and the second attenuation amount. This is because, when the operation part 60 calculates the concentration of the gas to be measured based on the first attenuation amount and the second attenuation amount, it is always affected by the attenuation amount with worse SNRs. Therefore, the difference between the first optical path length $l_1$ of infrared light guided by the first light guide part 21 and the second optical path length $l_2$ of infrared light guided by the second light guide part 22 is preferably 0% or more and 5% or less of the first optical path length $l_1$ when the relationship $l_1 \geq l_2$ is satisfied where the first optical path length $l_1$ is equal to or longer than the second optical path length $l_2$. Alternatively, the difference between the first optical path length $l_1$ of infrared light guided by the first light guide part 21 and the second optical path length $l_2$ of infrared light guided by the second light guide part 22 is preferably 0% or more and 5% or less of the second optical path length $l_2$ when the relationship $l_2 \geq l_1$ is satisfied where the second optical path length $l_2$ is equal to or longer than the first optical path length $l_1$. Further, when there is no difference between the first optical path length $l_1$ of infrared light guided by the first light guide part 21 and the second optical path length $l_2$ of infrared light guided by the second light guide part 22, it is preferable because there is no difference in SNR between the first attenuation amount and the second attenuation amount caused by the difference in optical path length.

[Drive Part]

The drive part 70 supplies a drive current or a drive voltage for driving or stopping the first light source 31 to the first light source 31. For example, when stopping the first light source 31, the drive part 70 supplies the same voltage to the anode electrode of the first light source 31 and the cathode electrode of the first light source 31. For example, when driving the first light source 31, the drive part 70 supplies different voltages to the anode electrode of the first light source 31 and the cathode electrode of the first light source 31. The drive current signal or drive voltage signal output from the drive unit 70 or driving or stopping the first light source 31 may be used when the operation part 60 performs calculation.

Further, the drive part 70 supplies a drive current or a drive voltage for driving or stopping the second light source 32 to the second light source 32. For example, when stopping the second light source 32, the drive part 70 supplies the same voltage to the anode electrode of the second light source 32 and the cathode electrode of the second light source 32. For example, when driving the second light source 32, the drive part 70 supplies different voltages to the anode electrode of the second light source 32 and the cathode electrode of the second light source 32. The drive current signal or drive voltage signal output from the drive unit 70 for driving or stopping the second light source 32 may be used when the operation part 60 performs calculation.

The drive part 70 includes, for example, a power supply device, an amplifier, and the like. The drive part 70 may be integrated into the operation part 60, or separated therefrom. Further, the drive part 70 may be mounted on the substrate 80 or provided outside the substrate 80.

[Substrate]

The substrate 80 mounts the first light guide part 21, the second light guide part 22, the first light source 31, the second light source 32, the first optical filter 41, the second optical filter 42, the first light receiving part 51, the second light receiving part 52, the operation part 60, the drive part 70, and the like. The substrate 80 electrically connects various electronic components mounted thereon. The operation part 60 and the drive part 70 may be provided outside the substrate 80.

The substrate 80 is preferably formed of a material having phenolic resin, epoxy resin, polyimide resin, alumina resin, and the like, such as FR-1, FR-2, FR-3, FR-4, FR-5, GPY, CEM-1 and CEM-3.

The first light source 31, the second light source 32, the first light receiving part 51 and the second light receiving part 52 may preferably be mounted on the same substrate. When these members are mounted on the same substrate, a substrate is not needed to be prepared for each member, and thus the manufacturing cost can be reduced, and the measuring accuracy can be improved.

In the optical concentration measuring device 1 according to the present embodiment, the difference between the peak wavelength of the first effective sensitivity spectrum and the peak wavelength of the second effective sensitivity spectrum is 0.2 times or more and 0.8 times or less the full width at half maximum of the first effective sensitivity spectrum, and the operation part 60 performs the interference removal operation described above. In this manner, the effect of absorption of infrared light by interference gas can be removed without completely separating the transmission bands of two optical filters, as with the known optical concentration measuring device, and further, even if the wavelength band in which the gas to be measured absorbs infrared light is narrow, the amount of light received by the light receiving part can be drastically increased compared to the known optical concentration measuring device. Therefore, the optical concentration measuring device 1 capable of measuring the concentration of the gas to be measured with high accuracy while removing the effect of light absorption by the interference gas can be realized.

<Optical Concentration Calculating Method>

Next, an optical concentration measuring method according to the present embodiment will be described by using specific examples. For example, the case where the gas to be measured is methane and the interference gas is water vapor will be described.

First, the operation part 60 calculates the first attenuation amount of the first intensity of infrared light by gas to be measured and interference gas present in the first optical path $L_1$ based on the first detection signal output from the first light receiving part 51.

For example, the operation part 60 calculates the first attenuation amount of the first intensity of infrared light by methane and water vapor present in the first optical path $L_1$ based on the first detection signal output from the first light receiving part 51. Assuming that the attenuation amount of the first intensity of infrared light by methane present in first optical path $L_1$ is $A1_{CH_4}$ and the attenuation amount of the first intensity of infrared light by water vapor present in the first optical path $L_1$ is $B1_{H_2O}$, the first attenuation amount $\Delta I\_1$ is expressed by the following equation (3).

$$\Delta I\_1 = A1_{CH_4} + B1_{H_2O} \tag{3}$$

Next, the operation part 60 calculates the second attenuation amount of the second intensity of infrared light by gas to be measured and interference gas present in the second optical path $L_2$ based on the second detection signal output from the second light receiving part 52.

For example, the operation part 60 calculates the second attenuation amount of the second intensity of infrared light by methane and water vapor present in the second optical path $L_2$ based on the second detection signal output from the second light receiving part 52. Assuming that the attenuation amount of the second intensity of infrared light by methane present in the second optical path $L_2$ is $A2_{CH_4}$ and the attenuation amount of the second intensity of infrared light by water vapor present in the second optical path $L_2$ is $B2_{H_2O}$, the second attenuation amount $\Delta I\_2$ is expressed by the following equation (4).

$$\Delta I\_2 = A2_{CH_4} + B2_{H_2O} \tag{4}$$

Originally, there is a higher-order absorption term that indicates the effects of both methane and water vapor, but the absorption amount of water vapor is small enough to be expressed by the Maclaurin expansion. Therefore, higher-order absorption terms can be ignored.

Next, the operation part 60 calculates the concentration of gas to be measured based on the first attenuation amount and the second attenuation amount. As described above, the attenuation amount of the first intensity of infrared light by interference gas present in the first optical path $L_1$ and the attenuation amount of the second intensity of infrared light by interference gas present in the second optical path $L_2$ are in a proportionate relationship.

Therefore, first, the operation part 60 subtracts the second attenuation amount from the amount obtained by multiplying the first attenuation amount by a proportional constant, and removes the attenuation amount of the first intensity of infrared light by interference gas present in the first optical path $L_1$ and the attenuation amount of the second intensity of infrared light by interference gas present in the second optical path $L_2$ to perform the interference removal operation in which the effect of infrared light by interference gas is removed. Alternatively, the operation part 60 subtracts the first attenuation amount from the amount obtained by multiplying the second attenuation amount by a proportional constant, and removes the attenuation amount of the first intensity of infrared light by interference gas present in the first optical path $L_1$ and the attenuation amount of the second intensity of infrared light by interference gas present in the second optical path $L_2$ to perform the interference removal operation in which the effect of infrared light by interference gas is removed. In this manner, the operation part 60 can calculate the concentration of gas to be measured even if the concentration of interference gas is unknown.

For example, the operation part 60 multiplies the equation (3) by the proportional constant C, and subtracts the equation (4) from the equation obtained by multiplying the equation (3) by the proportional constant. Since the attenuation amount $B1_{H_2O}$ of the first intensity of infrared light by water vapor present in the first optical path $L_1$ and the attenuation amount $B2_{H_2O}$ of the second intensity of infrared light by water vapor present in the second optical path $L_2$ are in a proportional relationship, the following equation (5) holds.

$$B1_{H_2O} \times C = B2_{H_2O} \quad (5)$$

Therefore, the operation part 60 can remove the attenuation amount $B1H_2O$ of the first intensity of infrared light by water vapor present in the first optical path $L_1$ and the attenuation amount $B2H_2O$ of the second intensity of infrared light by water vapor present in the second optical path $L_2$ by subtracting the equation (4) from the equation obtained by multiplying the equation (3) by the proportional constant C. The operation part 60 can perform an interference removal operation that leaves only the information on the attenuation amount of the intensity of infrared light by methane by canceling the information on the attenuation amount of the intensity of infrared light by water vapor.

For example, the operation part 60 multiplies the equation (4) by the proportional constant C', and subtracts the equation (3) from the equation obtained by multiplying the equation (4) by the proportional constant. Since the attenuation amount $B1H_2O$ of the first intensity of infrared light by water vapor present in the first optical path $L_1$ and the attenuation amount $B2H_2O$ of the second intensity of infrared light by water vapor present in the second optical path $L_2$ are in a proportional relationship, the following equation (6) holds.

$$B1_{H_2O} = B2_{H_2O} \times C' \quad (6)$$

Therefore, the operation part 60 can remove the attenuation amount $B1H_2O$ of the first intensity of infrared light by water vapor present in the first optical path $L_1$ and the attenuation amount $B2H_2O$ of the second intensity of infrared light by water vapor present in the second optical path $L_2$ by subtracting the equation (3) from the equation obtained by multiplying the equation (4) by the proportional constant C'. The operation part 60 can perform a removal operation that leaves only the information on the attenuation amount of the intensity of infrared light by methane by canceling the information on the attenuation amount of the intensity of infrared light by water vapor.

Finally, the operation part 60 calculates the concentration of the gas to be measured by applying the concentration calculation table or the fitting of exponential function to the output after the interference removal operation in which the effect of infrared light absorption by interference gas is removed. It is preferable that the operation part 60 calculates the concentration of gas to be measured by using a polynomial of third order or higher in the equation (2). In this manner, the operation part 60 can calculate the concentration of gas to be measured easily with high accuracy.

In the optical concentration measuring method according to the present embodiment, an interference removal operation in which the effect of absorption of infrared light by interference gas is removed is performed by using the fact that, when a difference between the peak wavelength of the first effective sensitivity spectrum and the peak wavelength of the second effective sensitivity spectrum is defined to be 0.2 times or more and 0.8 times or less of the full width at half maximum of the first effective sensitivity spectrum, the attenuation amount of the first intensity of infrared light by interference gas present in the first optical path and the attenuation amount of the second intensity of infrared light by interference gas present in the second optical path are in a proportional relationship. The optical concentration measuring device 1 that applies the above-described optical concentration measuring method can measure the concentration of gas to be measured with high accuracy while removing the effect of absorption of light by interference gas.

<Variation>

In this description, explanation was made by selecting Gaussian as a function showing the intensity distribution of the effective sensitivity spectrum illustrated in FIG. 4, but the function showing the intensity distribution of the effective sensitivity spectrum is not limited to this. For example, Lorenz function may be selected. Further, the wavelength characteristics of the light source or the optical path were not mentioned as an explanation of the principle of the interference removal operation, but the same result can be obtained even if these wavelength characteristics are included. For example, Planck's law, which represents the wavelength distribution of infrared light emitted from a light source, may be multiplied to include the wavelength characteristics of the light source. Further, the status density distribution function may be multiplied by the reflectance characteristics of the optical element to include the wavelength characteristics of the light source and the optical path.

Further, in this description, an example where the number of interference gases is one is described, but the number of interference gases is not limited to one, and a plurality of interference gases may be existed. Even if a plurality of interference gases are existed, since the attenuation amount of the first intensity of infrared light by each interference gas and the attenuation amount of the second intensity of infrared light by each interference gas are in a proportional relationship, an interference removal operation in which the attenuation amount of the first intensity of infrared light by each interference gas and the attenuation amount of the second intensity of infrared light by each interference gas are removed can b e performed by applying the above described calculation method. In other words, the optical concentration measuring device 1 can measure the concentration of the gas to be measured with high accuracy while removing the effect of light absorption by the interference gas, whether the number of interference gases is one or more.

<Other Variations>

Further, an optical concentration measuring device that does not include an operation part as an essential component is construed as an independent embodiment as a module for optical concentration measuring device.

Application of Embodiment

The optical concentration measuring device 1 according to the present embodiment can be applied to a variety of devices. For example, the optical concentration measuring device 1 can be applied to devices that detect leakage of natural gas in the pipeline for transferring natural gas, devices for detecting the concentration of the gas contained in the means of transportation such as automobiles, trains and airplanes, devices for detecting concentrations of specific gases, and the like.

The above described embodiment has been described as a representative example, but it will be apparent to one of ordinary skill in the art that numerous modifications and replacements can be made within the spirit and scope of the present invention. Therefore, the present invention should not be interpreted as being restricted to the above embodiment. A variety of changes and modifications may be made without departing from the scope of the appended claims. For example, a plurality of the structural blocks indicated in the configuration diagrams of the embodiment may be combined into one, or one structural block may be divided into multiple parts. For example, the order of each operation described in the embodiments is not limited to the above and can be changed as appropriate.

The invention claimed is:

1. An optical concentration measuring device configured to measure concentration of a gas to be measured contained in a mixture of the gas to be measured and an interference gas, comprising:
   a first light source configured to emit infrared light;
   a first optical filter having a first transmission band that is a wavelength band including a wavelength at which the gas to be measured and the interference gas absorb the infrared light;
   a first light receiving part that has a sensitivity in the first transmission band and outputs a first detection signal according to a first intensity of light received;
   a first light guide part configured to guide the infrared light to the first light receiving part;
   a second light source configured to emit the infrared light;
   a second optical filter having a second transmission band that is a wavelength band including a wavelength at which the gas to be measured and the interference gas absorb the infrared light;
   a second light receiving part that has a sensitivity in the second transmission band and outputs a second detection signal according to a second intensity of light received;
   a second light guide part configured to guide the infrared light to the second light receiving part; and
   an operation part configured to calculate a first attenuation amount of the first intensity by the gas to be measured and the interference gas based on the first detection signal, a second attenuation amount of the second intensity by the gas to be measured and the interference gas based on the second detection signal, and concentration of the gas to be measured based on the first attenuation amount and the second attenuation amount, wherein
   a difference between a peak wavelength of a first effective sensitivity spectrum based on the first transmission band in the first light receiving part and a peak wavelength of a second effective sensitivity spectrum based on the second transmission band in the second light receiving part is ±0.2 times or more and ±0.8 times or less of a full width at half maximum of the first effective sensitivity spectrum,
   wherein the operation part subtracts the second attenuation amount from an amount obtained by multiplying the first attenuation amount by a proportional constant or subtracts the first attenuation amount from an amount obtained by multiplying the second attenuation amount by a proportional constant different from the above proportional constant to remove an attenuation amount of the first intensity by the interference gas and an attenuation amount of the second intensity by the interference gas.

2. The optical concentration measuring device according to claim 1, wherein a full width at half maximum of the first effective sensitivity spectrum or the second effective sensitivity spectrum is 80 nm or more and 300 nm or less.

3. The optical concentration measuring device according to claim 1, wherein a central wavelength of the first transmission band is 3.2 μm or more and 3.4 μm or less.

4. The optical concentration measuring device according to claim 1, wherein, when a first optical path length of the infrared light guided by the first light guide part is longer than a second optical path length of the infrared light guided by the second light guide part, a difference between the first optical path length and the second optical path length is 0% or more and 5% or less of the first optical path length.

5. The optical concentration measuring device according to claim 1, wherein, when a second optical path length of the infrared light guided by the second light guide part is longer than a first optical path length of the infrared light guided by the first light guide part, a difference between the first optical path length and the second optical path length is 0% or more and 5% or less of the second optical path length.

6. The optical concentration measuring device according to claim 1, wherein the first light source is identical to the second light source.

7. The optical concentration measuring device according to claim 1, wherein the first light source and the second light source or the first light receiving part and the second light receiving part are composed of a semiconductor or a compound semiconductor.

8. A module for optical concentration measuring device configured to measure concentration of a gas to be measured contained in a mixture of the gas to be measured and an interference gas, comprising:
   a first light source configured to emit infrared light;
   a first optical filter having a first transmission band that is a wavelength band including a wavelength at which the gas to be measured and the interference gas absorb the infrared light;
   a first light receiving part that has a sensitivity in the first transmission band and receives light transmitted through the first optical filter;
   a first light guide part configured to guide the infrared light to the first light receiving part;
   a second light source configured to emit the infrared light;
   a second optical filter having a second transmission band that is a wavelength band including a wavelength at which the gas to be measured and the interference gas absorb the infrared light;
   a second light receiving part that has a sensitivity in the second transmission band and receives light transmitted through the second optical filter; and
   a second light guide part configured to guide the infrared light to the second light receiving part, wherein
   a difference between a peak wavelength of a first effective sensitivity spectrum based on the first transmission band in the first light receiving part and a peak wavelength of a second effective sensitivity spectrum based on the second transmission band in the second light receiving part is ±0.2 times or more and ±0.8 times or less of a full width at half maximum of the first effective sensitivity spectrum.

9. An optical concentration measuring method for an optical concentration measuring device configured to measure concentration of a gas to be measured contained in a mixture of the gas to be measured and an interference gas, the optical concentration measuring device comprising:
   a first light source configured to emit infrared light;
   a first optical filter having a first transmission band that is a wavelength band including a wavelength at which the gas to be measured and the interference gas absorb the infrared light;
   a first light receiving part that has a sensitivity in the first transmission band and outputs a first detection signal according to a first intensity of light received;

a first light guide part configured to guide the infrared light to the first light receiving part;

a second light source configured to emit the infrared light;

a second optical filter having a second transmission band that is a wavelength band including a wavelength at which the gas to be measured and the interference gas absorb the infrared light;

a second light receiving part that has a sensitivity in the second transmission band and outputs a second detection signal according to a second intensity of light received;

a second light guide part configured to guide the infrared light to the second light receiving part; and an operation part, wherein a difference between a peak wavelength of a first effective sensitivity spectrum based on the first transmission band in the first light receiving part and a peak wavelength of a second effective sensitivity spectrum based on the second transmission band in the second light receiving part is ±0.2 times or more and ±0.8 times or less of a full width at half maximum of the first effective sensitivity spectrum, the method comprising the steps of:

calculating, by the operation part, a first attenuation amount of the first intensity by the gas to be measured and the interference gas based on the first detection signal;

calculating, by the operation part, a second attenuation amount of the second intensity by the gas to be measured and the interference gas based on the second detection signal; and calculating, by the operation part, concentration of the gas to be measured based on the first attenuation amount and the second attenuation amount, wherein the step of calculating concentration of the gas to be measured includes the step of subtracting, by the operation part, the second attenuation amount from an amount obtained by multiplying the first attenuation amount by a proportional constant, or the first attenuation amount from an amount obtained by multiplying the second attenuation amount by a proportional constant different from the above proportional constant to remove an attenuation amount of the first intensity by the interference gas and an attenuation amount of the second intensity by the interference gas.

* * * * *